United States Patent [19]

Geraci

[11] 4,266,663
[45] May 12, 1981

[54] SURGICAL DRAPE FOR AN OPERATING MICROSCOPE

[75] Inventor: James L. Geraci, Cincinnati, Ohio

[73] Assignee: Carl Zeiss, Inc., New York, N.Y.

[21] Appl. No.: 93,178

[22] Filed: Nov. 13, 1979

[51] Int. Cl.³ .................. B65D 85/38; B65D 65/04; B65D 65/28; G02B 27/00

[52] U.S. Cl. .................. 206/223; 150/52 R; 206/305; 206/634; 206/316; 350/61; 350/65

[58] Field of Search ............... 206/305, 316, 634, 223; 150/52 R; 350/65, 61

[56] References Cited

U.S. PATENT DOCUMENTS

| | | | |
|---|---|---|---|
| 3,528,720 | 9/1970 | Treace | 206/305 |
| 3,542,450 | 11/1970 | Terhune | 350/65 |
| 3,698,791 | 10/1972 | Walchle et al. | 350/61 |
| 4,045,118 | 8/1977 | Geraci | 350/61 |

Primary Examiner—William T. Dixson, Jr.
Attorney, Agent, or Firm—Hopgood, Calimafde, Kalil, Blaustein & Lieberman

[57] ABSTRACT

The invention contemplates a disposable surgical drape of pliable elastomeric film, precut and seamed for sterile packaging and instant readiness to assemble to a microscope head, with assurance of microscope sterility during surgical procedures. The drape is so formed as to enable simple and effective lens barrels, without requiring use of rubber bands, pressure-sensitive tape, adhesive bands or the like. A kit including one disposable drape also includes an objective-lens adapter ring which not only correctly retains drape material at the periphery of an objective-lens barrel, but also provides a rugged base, external of the drape, for ready removable mounting of successive disposable plane-parallel protective cover plates as they may become soiled in the course of any single surgical procedure.

24 Claims, 9 Drawing Figures

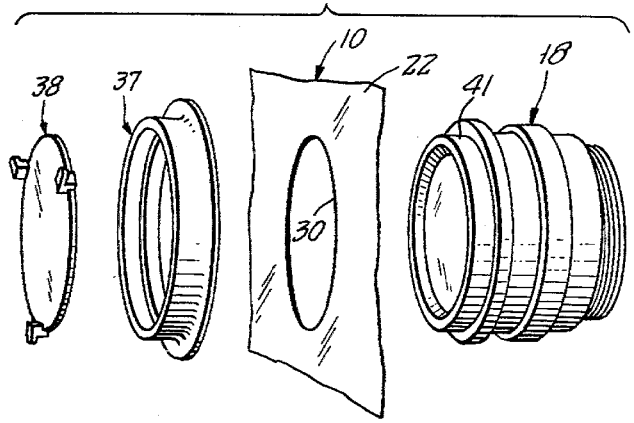
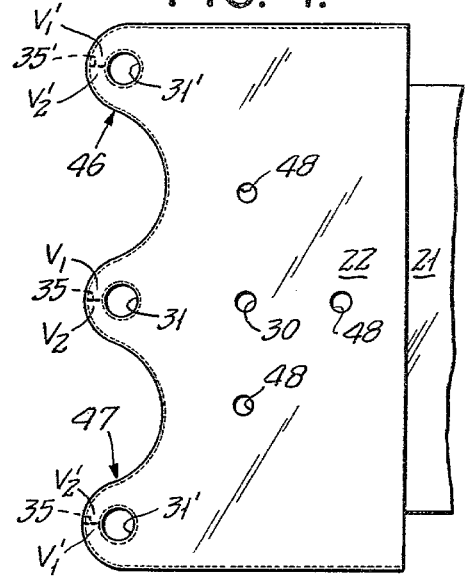
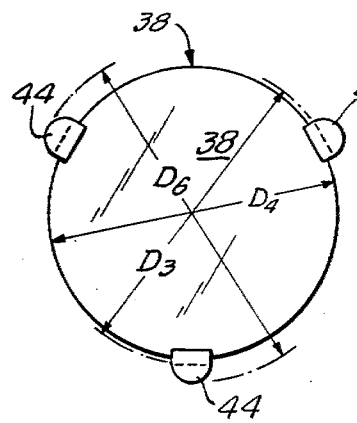
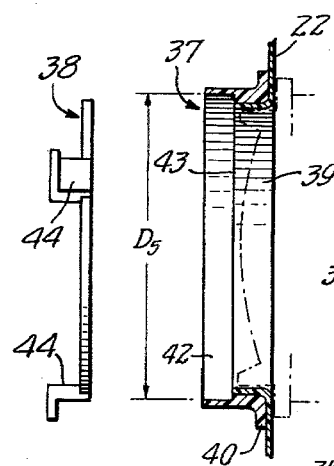
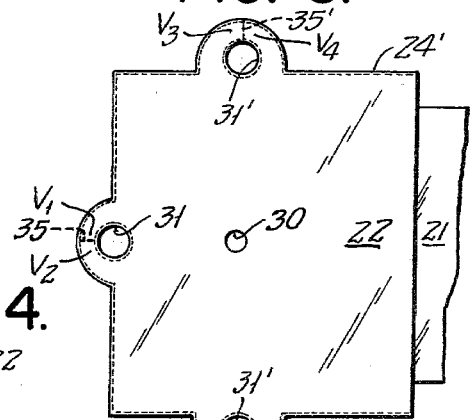
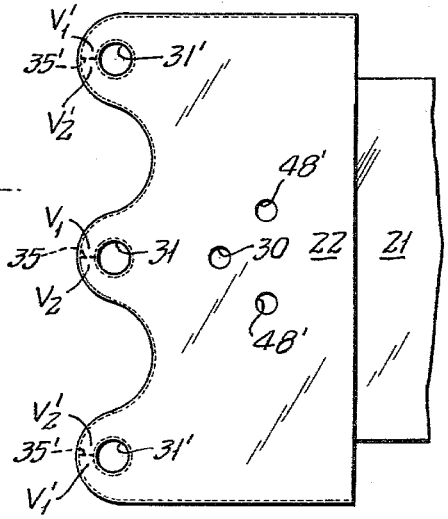

4,266,663

SURGICAL DRAPE FOR AN OPERATING MICROSCOPE

BACKGROUND OF THE INVENTION

The invention relates to a disposable-drape construction for use as a sterile cover for a microscope in the course of a surgical operating procedure.

Disposable drapes of the character indicated have been disclosed in various issued patents, notably U.S. Pat. Nos. 3,528,720 (Treace), No. 3,542,450 (Terhune), No. 3,698,791 (Walchle, et al.), and No. 4,045,118 (Geraci). All of these schemes employ an elongated sleeve or sock of sterilized, thin, transparent plastic film, open at one end for substantially complete enveloping assembly over not only a microscope head unit, but also all the way along the articulated system of cantilevered arms by which the head is positioned at adjusted offset and elevation with respect to a fixed mount, such as a floor-mounted vertical column or stand. Tape, bands and the like are required to gather and retain excess sleeve material along the cantilevered arm structure; special fittings and elements are assembled to the drape to facilitate lens rim adaptation; special provision must be made for the exhaust of heat developed by the illuminator associated with the microscope; tear-off pieces must be disposed of when severed; and in general an excessive quantity of drape material is required. In one way or another, these are all disadvantages, inconveniences, and wasteful features of prior-art constructions.

BRIEF SUMMARY OF THE INVENTION

It is an object of the invention to provide an improved surgical drape of the character indicated, avoiding or materially reducing disadvantages, inconveniences and waste that have characterized prior constructions.

A specific object is to meet the above object with a construction involving and requiring no appendages to the drape film assembly per se, when packed for storage, in readiness for use, thus making for compact storage and low-cost construction.

Another specific object is to provide improved ocular-adaptation structural features in such a drape.

A further specific object is to provide improved objective-lens adaptation features in such a drape.

It is also a specific object to provide simplified disposable protective cover plate structure removably adaptable to protect the objective lens, in the context of a surgically draped microscope of the invention.

Still another object is to provide an improved surgical drape preformed with structural features adaptable to a variety of microscope ocular combinations and configurations.

The foregoing objects and various further features of novelty are achieved by the invention, wherein a disposable surgical drape of pliable elastomeric film is precut and seamed for sterile packaging and instant readiness to assemble to a microscope head. The drape comprises upper and lower panels which register and are seamed to define a bag-like configuration which is primarily and assuredly adapted to provide full closure of the front, sides, top and bottom of the microscope head, leaving an elongate tail extension of the upper panel as the only cover, a gravitationally draped cover, for such cantilevered support-arm structure as may be employed to mount the microscope head. A particular combination of local seamed-edge contouring, in conjunction with the seamed peripheral margin of nearby registering apertures, in the two panels, enables suitable individual sleeve-like enclosures to be selectively available for assembly to the respective ocular barrels of a binocular viewing assembly, merely by tearing along an alignment that has been weakened by perforation slits. Various other features of simplicity and convenience are embodied in the drape, without requiring structural addition to the film panels of the drape per se.

DETAILED DESCRIPTION

Preferred embodiments of the invention will be illustratively described in conjunction with the accompanying drawings, in which:

FIG. 3 is an enlarged exploded view in perspective of objective-lens adapter and removable cover-plate structure adapted to part of the drape assembly of FIG. 1;

FIG. 4 is a vertical sectional view of the adapter of FIG. 3;

FIGS. 5 and 6 are, respectively, front-elevation and side-elevation views of the removable cover plate of FIG. 3; and FIGS. 7, 8 and 9 are partly broken-away plan views similar to FIG. 2, to illustrate modifications.

Figure 1:
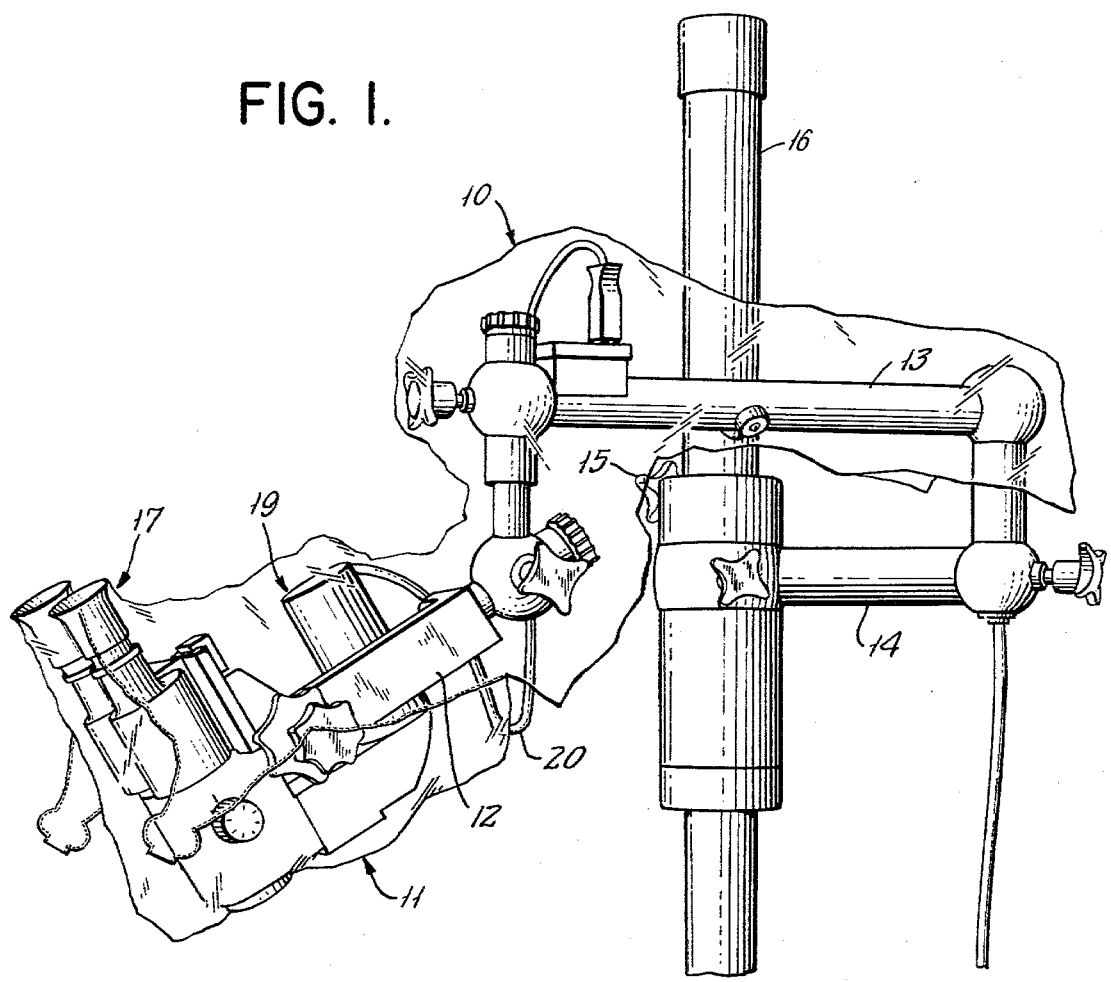
FIG. 1 is a simplified view in perspective for the head unit and the cantilevered support-arm structure of an operating microscope, shown with a surgical drape assembly of the invention installed thereon.
Figure 2:
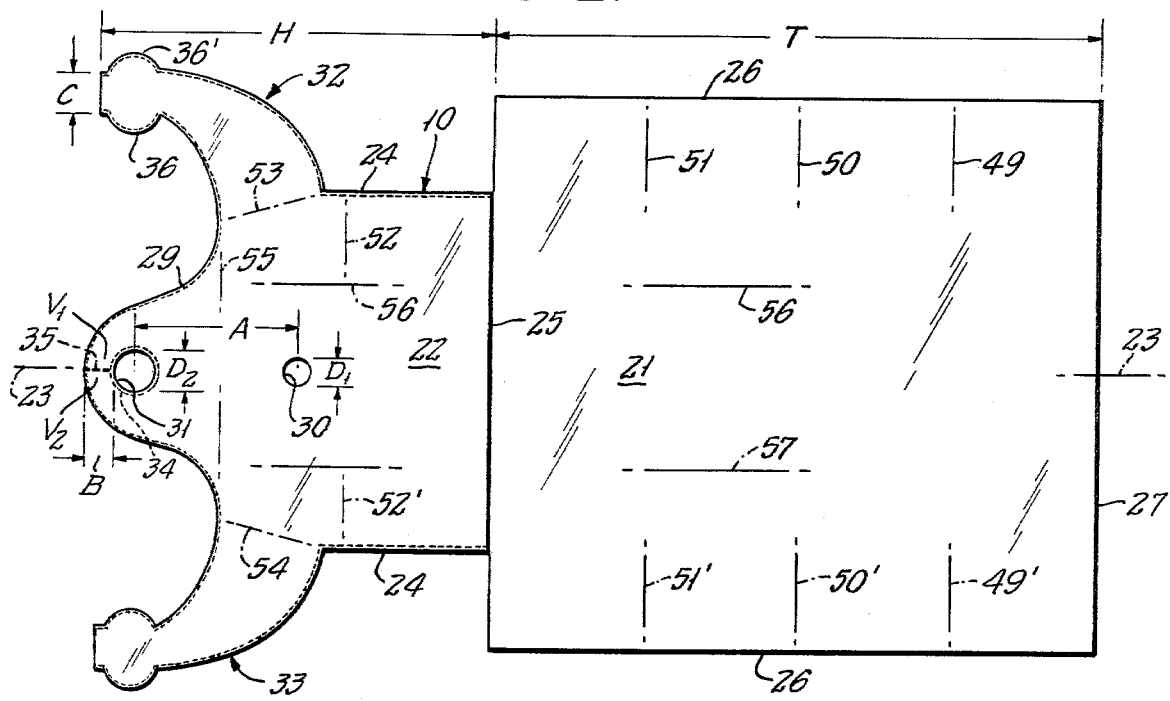
FIG. 2 is a plan view of the underside of the drape assembly of FIG. 1.

The surgical drape 10 of FIG. 2 is shown in FIG. 1 in application to an operating microscope, comprising a head unit 11, supported at the cantilevered end of a succession of selectively clamped articulated arms 12-13-14. Head unit 11 and arms 12-13-14 are selectively clamped by means 15 to desired vertical positioning on a floor-mounted column 16. The head unit 11 comprises a pair of binocular-viewing oculars 17 and associated microscope structure including an objective lens 18 (FIG. 3) and an illuminator 19, for which flexible electrical-supply cable 20 is carried by the arm structure. It will be understood that the head unit 11 may additionally incorporate one or more side-mounted monoculars, further binocular-viewing oculars, or the like, depending upon operational requirements.

Referring to FIG. 2, the drape 10 is illustratively a connected assembly of but two parts, being an upper panel 21 and a lower panel 22, both of suitably soft, pliant, thin elastomeric plastic film, being preferably a polyolefin film such as the copolymer polypropylene product of Crown Zellerbach, known as "Crown Zeelon 320", of 1.0-mil thickness. This particular material has a temperature tolerance and elastomeric, antistatic, and anti-crackle properties which render it highly satisfactory for surgical-drape applications. The planiform of the drape 10 has lateral symmetry about a central longitudinal axis 23, which extends over a head region (dimensionally designated H) and a tail region (dimensionally designated T). The upper and lower panels 21-22 have registering profiles over the extent H of the head region, but it is only the upper panel 21 which extends rearwardly for the extent T of the tail region. For want of a better term, I say that the registering head regions of the respective panels 21-22 are generally rectangular, being defined by and between lateral limiting edges 24, by a front limiting edge of special contour (to be described), and by the rear limiting edge 25 of the lower panel 22. The upper panel is a one-piece integrally connected shape comprising the just-described head region, plus a rectangular tail region defined by lateral edges 26 and a rear edge 27. The lateral limiting edges and the contoured front limiting edge of the described head-region configuration are connected, as by heat-seaming suggested by thin dashed lines 28 just inside the marginal edges involved. The panels 25 are, however, not connected at the rear edge of the head region, and so the assembly consists of a rearwardly openable pliant bag, with an elongate tail. The bag portion envelops the head unit 11 (and its adjacent support arm 12), while the tail region of upper panel 21 is merely laid along and allowed to gravitationally drape over both sides of the articulated arm structure 13-14, to or near connection to the vertical column 16.

The head region of the drape is specially characterized for somewhat universal optional adaptation to a variety of ocular and objective circumstances which may exist or be desired for particular operating microscope procedures. These characterizing features involve no additional parts for the assembled drape panels 21-22, but in the form of FIG. 2 involve a central circular opening 30 in the lower panel only, and registering circular openings 31 in both panels 21-22 near but offset from the contoured front limiting edge 29 of the head-adaptable configuration of the drape. Like but oppositely directed tapering projections 32-33 characterize the convergence of lateral limiting edges 24 with the contoured front limiting edge and will be later more fully described. The opening 30 is of a diameter $D_1$ sized for interference with the outside diameter of the front rim of the objective-lens barrel and will be later more fully described. The registering openings 31 are part of a formation to adapt to both of the oculars 17 and will now be described.

Since openings 31 are part of a formation to accommodate the oculars 17, the longitudinal offset A from opening 30 should be of ample length, for example 11 inches, to accept the most extreme dimensional set-up of the microscope at head unit 11. The panels 21-22 are connected to each other at their registering peripheries of openings 31, as by heat-seaming suggested by light dashed lines 34, and the front limiting edge 29 near openings 31 is characterized by forward convex arcuate bowing at closest offset B from openings 31, the offset B being on the central axis 23. Laterally outward from the offset B, the arcuate convex contour expands in its offset from openings 31, being eventually merged into the concave arcuate formation of part of the applicable one of the front corner projections 32-33. A heavy dashed line 35 denotes a locally weakened, tearable region of the connected panels 21-22, being suitably an alignment of spaced longitudinal slits through both panels.

In use, i.e., when an initial application of the head-region bag has been made over the head unit 11, and with the upper panel 21 uppermost, one simply pulls laterally at the openings 31 to break the front limiting edge 29 at the perforations 35, thereby defining two like projecting formations $V_1$-$V_2$, each of which is unsecured and therefore open where they have been severably related at alignment 35. In all other respects, formations $V_1$-$V_2$ are convergent and tubular by reason of seamed connection of panels 21-22 at their registering front limiting edges and at the rim of their registering circular openings 31. Therefore, each of the formations $V_1$-$V_2$ may be readily manipulated to fit over and to the outer rim of a different one of the viewing oculars 17. To accomplish the foregoing, the effective offset B between front-edge and circular edge (34) seams is preferably substantially equal to half the circumference of the rim of an ocular barrel, and if the effective offset B is slightly less, than the end opening of each formation $V_1$($V_2$) can be elastically stretched for tensed sealing retention to the applicable ocular-lens barrel. I have found an opening (31) diameter $D_2$ of 3 inches perfectly adequate to assure an unimpeded full range of interpupilary adjustment of the binocular-viewing oculars 17, in the described drape application of formations $V_1$-$V_2$ thereto.

Each of the corner projections 32-33 is adapted for sock-like application to a monocular-viewing tube, should the head unit be so equipped. Taking the projection 32 as illustrative, it is an arm of the drape assembly, at mutual approach of two converging edges, namely, a concave arcuate region of the front limiting edge and the nearby convex arcuate extension of a lateral limiting edge 24. The panels are secured along these converging edges, but at their outer end they terminate at a minimum span C of locally unsecured edge, the span C being substantially one half the circumference of the outer rim of a monocular. Preferably, each of the convergent arcuate edges of projection 32 includes one of a pair of opposed local lobes 36-36', to permit pinched grasping of these lobes for more ready application over the monocular involved, as will be understood.

The final operation to complete application of the bag portion of the drape to the head unit 11 involves a secure fitting of the circular aperture 30 to the rim of the objective-lens barrel. This operation involves additional parts 37-38, shown and to be described in connection with FIGS. 3, 4, 5 and 6. As best seen in FIGS. 3 and 4, the part 37 is a flanged ring, which may be of suitable injection-molded plastic such as polystyrene; and the part 38 is a replaceable cover plate, again injection-molded, but preferably of optically clear acrylic material. Ring 37 has a bore 39 which flares at rounded-corner juncture with a reinforcing flange 40, at one axial end; bore 39 is sized for interference fit to the outside diameter of the rim 41 of the barrel of objective lens 18, when the thickness of lower panel 22 is interposed. At its other axial end, ring 37 has a counterbore 42 which establishes a shouldered seat 43 to which the replaceable cover plate 38 can locate. At the same time, counterbore 42 makes for a thin compliant sleeve-like periphery of the ring 37, whereby local radial deflection of the sleeve formation upon insertion of cover plate 38 is operative to retain plate 38, when abutted to the seat 43. With lower panel 22 so positioned over the objective lens 18 that opening 30 is within the rim 41, i.e., with panel material around opening 30 and within the limits of rim 41, ring 37 is axially applied, thereby locally elastomerically deforming the panel material and establishing a secure, peripherally sealed mount of the ring 37 to the objective-lens barrel. Ring 37 then constitutes an externally accessible adapter mount, for removable reception of the cover plate 38.

As shown in FIGS., 3, 5, and 6, the cover plate 38 comprises a circular-disc body, including plural spaced peripheral mounting feet 44 integrally formed therewith. The opposed faces of the disc body of plate 38 are plane-parallel, so as to introduce no impairment of microscope functions. Each of the feet 44 comprises an axially extending portion of thickness extending to a geometrical circle of diameter $D_3$ which exceeds the diameter $D_4$ of the plane-parallel disc body, and diameters $D_3$-$D_4$ are selected to respectively interfere with and clear the diameter $D_5$ of counterbore 42. Finally, a radially outward tab at the axially outer end of each of the feet 44 serves for convenience in manual grasping, and is located at such effective offset from the disc body as to equal or exceed the depth of counterbore 42; and the maximum unstressed diameter $D_6$ of the geometrical circle for these tabs is in excess of the outer diameter of rings 37 at the sleeve-like region of counterbore 42. Upon insertion of a cover plate 38 at counterbore 42, the sleeve-like region surrounding the counterbore is locally and transiently deformed at spaced points by reason of the $D_3$-$D_5$ interference. In the course of an operating procedure, a soiled cover plate 38 is readily removed by grasping the tabs of feet 44, and a fresh clear plate 38 is installed just as readily.

FIG. 7 illustrates a modification of the drape of FIG. 2, in the sense that the registering head regions of panels 21-22 are contoured and otherwise formed and secured at their connected front limiting edge, so as to provide for further binocular-viewing adaptability at lateral offset to one or the other or both sides of the central axis 23 of longitudinal symmetry of the drape. In this connection, convex arcuate front-edge profiles at 46-47 closely resemble the central contouring already described for $V_1$-$V_2$ in FIG. 2, in conjunction with registering apertures 31 of FIG. 2. For this reason, these and other corresponding parts are given the same numbers with primed notation at 46-47 in FIG. 7. FIG. 7 further illustrates the provision of an additional pair of openings 48 at locations of equal and opposite offset laterally from the objective-lens opening 30, and formed only in the lower panel 22, for use in the event that clear light transmission is needed for the illuminator, and regardless of the lateral offset to which the illuminator may be positioned for a particular microscope-head set-up, it being understood that adapter-ring and replaceable cover-plate elements, as described in connection with FIGS. 3 to 6, may be applied at the applicable opening 48 to enable ready cover-plate installation and replacement for protection of the objective-lens and its associated barrel structure, as well as for similar protection of the corresponding illuminator lens and its associated barrel structure.

The modification of FIG. 8 resembles that of FIG. 7 except that the further binocular-viewing ocular accommodation by the drape is located generally centrally along the respective lateral limiting edges 24' of the head-unit end of the drape assembly. Severance along one of the perforations 35' will make available two tubular projections $V_3$-$V_4$ for assembly to oculars of a binocular-viewing system on one side of the head unit 11, while such severance at 35' on the other lateral side will make the pair $V_3'$-$V_4'$ available for a similar purpose.

The arrangement of FIG. 9 is identical to that of FIG. 7, except that the additional pair of openings 48' (in lower panel 22 only) is not only offset laterally from the central opening 30, but is also offset rearwardly thereof. This arrangement will be appreciated as accommodating illuminator lens-barrel positioning which is similarly offset with respect to the objective-lens placement in a given head-unit configuration.

The described drape constructions will be seen to meet all stated objects, providing a range of adaptability to various possible complexities and asymmetries of multiple-viewing and of illuminator placement. Since the drape comprises only pliant panels 21-22, the described configurations lend themselves to simple folding which further facilitates application to an operating microscope. In FIG. 2, such folds are suggested by fold creasing first at alignment 49-49', whereby the rear limiting edge 27 may be folded over the upper surface of upper panel 21 and into substantial register with the next fold-crease alignment 50-50'. Successive similar folds at crease alignment 50-50' into substantial edge register with crease alignment 51-51', and then at crease alignment 51-51' into substantial edge register with the rear edge 25 of lower panel 22, bring the tail portion T of upper panel 21 into folded adjacency with the head-unit accommodating bag; whereupon, similar further successive folds at 25, and at crease alignment 52-52', bring all folds into overlap of the objective-lens accommodating region. The three projecting regions may be folded as along crease alignments 53-54-55 into the underside of the accumulated folds, whereupon all folds may be further compacted by laterally inward folding, say into thirds, along crease axis alignments 56-57, for stowage in a single pliant envelope (not shown). What was in its original flat condition about 60 inches long and 40 inches wide, is thus compressed by successive folds into a package of dimensions approximating $7\frac{1}{2}$ by $13\frac{1}{2}$ inches, which if further folded in half along the central axis 23 becomes very easily managed in envelope dimensions of 7 by 8 inches.

To apply the drape, one first unfolds enough to make the head-unit bag region openable, and applies the same over the front of the head unit 11, leaving the folded tail region of panel 21 folded until binocular adaptation is made at $V_1$-$V_2$. Thereafter, it is a simple matter to continue the unfolding of the tail region while gravitationally allowing the same to drape over the articulated arms 13-14. Objective-lens and illuminator-lens adapter fittings 37 are then applied, followed by cover plates 38, as applicable.

For ease of readability of engraved dial scales and settings on the microscope and other parts of the head unit 11, it is preferred that the film used for lower panel 22 be clear while that used for the upper panel 21 is embossed and color tinted.

In supplying the described drapes to hospitals, I prefer that the drape per se be but part of a kit which additionally includes, in the case of the drape 10 of FIG. 2 (or the drape of FIG. 8), one objective-lens adapter ring 37 and a plurality (such as five) removable cover plates 38. For drapes as in FIG. 7 or in FIG. 9, wherein illuminator-lens protection is also to be provided, I prefer a kit which includes the drape per se plus adapter rings 37 for the illuminator as well as the objective lens, together with a plurality of cover plates 38 for each of the two adapter rings.

While the invention has been described in detail for the preferred forms shown, it will be understood that modifications may be made without departure from the scope of the invention.

What is claimed is:

1. A disposable surgical drape for an operating microscope (a) having a binocular microscope head unit with two barrel-mounted viewing oculars and a barrel-mounted objective lens and (b) support structure including an elongate horizontal arm for cantilevered positioning of said head unit, said drape comprising connected upper and lower continuous panels of thin pliant elastomeric plastic sheet material, said panels having registering generally rectangular configuration at a head-unit adaptable region and being connected to each other along both lateral limiting edges of said configuration, such connection extending from front to rear limiting edges of said configuration and along said front limiting edge but to the exclusion of said rear limiting edge, said upper panel further including an elongate generally rectangular arm-adaptable region continuously and integrally formed with the rear limiting edge of said configuration and extending rearwardly of the rear limiting edge of said lower panel, said lower panel having a central circular aperture sized for interference with the rim diameter of the objective barrel, said configuration further comprising an ocular-adapting region characterized by registering apertures in both panels near but in offset relation to one of said connected limiting edges, said panels being further connected to each other at the perimeter of said registering apertures, and said panels being perforated along an alignment from said registering apertures to a near region of said one connected limiting edge, for ready simultaneous local separation of both panels at the perforation alignment, whereby upon severance at the perforation alignment, two spaced and now-openble tubular formations are immediately presented for direct separately protective manipulated assembly over the two binocular-viewing ocular barrels of the microscope.

2. A disposable surgical drape for an operating microscope having a binocular microscope head unit with two barrel-mounted viewing oculars and a barrel-mounted objective lens, said drape comprising connected upper and lower continuous panels of thin pliant elastomeric plastic sheet material, said panels having registering generally rectangular configuration at the head-unit-adaptable region and being connected to each other along both lateral limiting edges of said configuration, such connection extending from front to rear limiting edges of said configuration and along said front limiting edge but to the exclusion of said rear limiting edge, said lower panel having a central circular aperture sized for interference with the rim diameter of the objective barrel, said configuration further comprising an ocular-adapting region characterized by registering apertures in both panels near but in offset relation to one of said connected limiting edges, said panels being further connected to each other at the perimeter of said registering apertures, and said panels being perforated along an alignment from said registering apertures to a near region of said one connected limiting edge, for ready simultaneous local separation of both panels at the perforation alignment, whereby upon severance at the perforation alignment, two spaced and now-openable tubular formations are immediately presented for direct separately protective manipulated assembly over the two binocular-viewing ocular barrels of the microscope.

3. The drape of claim 2, in which said configuration is characterized by a convergent tapering arm projection at mutual approach of said front limiting edge and one of said lateral limiting edges, said panels being connected along side edges of said tapering arm projection, said latter connections being continuous but not beyond a locale of predetermined minimum separation of said side edges, said panels being unconnected over the separation span at said locale, said predetermined separation being so related to the rim circumference of a monocular barrel as to permit manipulated assembly of the thus-open end of the tapering arm projection over the rim of the monocular barrel.

4. The drape of claim 3, in which said configuration is further characterized by a second convergent tapering arm projection at mutual approach of said front limiting edge and the other of said later limiting edges, said panels being connected at said second tapering arm projection in correspondence with their connection at said first-mentioned tapering arm projection.

5. The drape of claim 2, in which said ocular-adapting region is disposed generally centrally along and with respect to said front limiting edge.

6. The drape of claim 2, in which said one connected limiting edge has a forwardly bowed arcuate profile local to said ocular-adapting region, said panels being continuously connected along said profile and said profile being symmetrically offset from the registering-apertures perimeter connection, the perforation alignment being effectively disposed at substantially the central plane of symmetry of said offset.

7. The drape of claim 2, in which said ocular-adapting region is one of two, along the same connected limiting edge of said configuration.

8. The drape of claim 2, in which said ocular-adapting region is one of two, each of which is along one of the two connected lateral edges of said configuration.

9. The drape of claim 2, in which said ocular-adapting region is one of two, along adjacent connected limiting edges of said configuration.

10. The drape of claim 2, in which said ocular-adapting region is one of three, at spaced locales along the connected front limiting edge of said configuration.

11. The drape of claim 2, in which to the exclusion of said upper panel said lower panel has a second circular aperture at lateral offset from said central circular aperture, said second circular aperture being sized for interference fit to the rim of the lens barrel of an illuminator associated with the head unit.

12. The drape of claim 11, in which said second circular aperture is one of two at equal and opposite lateral offsets from said central circular aperture.

13. The drape of claim 11, in which said second circular aperture is offset both laterally and rearwardly of said central circular aperture.

14. The drape of claim 12, in which both said second circular apertures are offset rearwardly as well as laterally of said central circular aperture.

15. The drape of claim 2, in which said lower panel is of clear transparent material.

16. The drape of claim 2, in which said upper panel is of color-tinted material and said lower panel is colorless and clear.

17. The drape of claim 2, in which said panels are of polypropylene.

18. A surgical-drape kit, comprising the drape of claim 2, and at least one objective-lens adapter ring, said ring having a bore which at least at on axial end is sized for interference fit with the objective-lens barrel when applied with the periphery of the central circular aperture of said lower panel interposed therebetween.

19. The kit of claim 18, in which the other axial end of said bore has a lens-receiving counterbore.

20. The kit of claim 19, and including at least one single-piece disposable plane-parallel transparent protective cover plate with an angularly spaced plurality of mounting feet sized for removably retained seating engagement with said ring and within said counterbore.

21. The kit of claim 20, in which said cover plate is but one of a plurality of like cover plates, whereby in the course of a single surgical operation a succession of clean cover plates may be readily installed to said ring without interfering with the ring attachment of said drape to the objective-lens barrel, thereby providing effectively continuous and unattenuated microscope viewing.

22. The kit of claim 20, in which the plurality of mounting feet is there.

23. The kit of claim 20, in which said plate is circular and of diameter less than the counterbore diameter, said feet projecting radially outward to interference-fit relation with the counterbore, and said feet each including an axial projection in the direction away from counterbore engagement, for manual-access and manipulation purposes.

24. The kit of claim 23, in which each axial projection terminates with a radially outward lug extending radially outward of the outside diameter of said ring, thereby facilitating lug engagement for cover-plate manipulation to the exclusion of said ring.

* * * * *